US012746012B2

(12) United States Patent
Kosiorek et al.

(10) Patent No.: US 12,746,012 B2
(45) Date of Patent: Sep. 29, 2026

(54) HEMORRHAGE CONTROL PLATE APPARATUS, SYSTEMS, AND METHODS

(71) Applicant: Alphapointe, Kansas City, MO (US)

(72) Inventors: Christopher B. Kosiorek, La Vernia, TX (US); Ryan Williams, Olathe, KS (US); Esra Abir, New York, NY (US); Christian D. Reid, Concord, NC (US); Jon R. Mattson, Harrisburg, NC (US); Christopher J. Murphy, Vass, NC (US); Corey F. Russ, Harrisburg, NC (US); Brenda Mee, West Newfield, ME (US); Faisal Ahmed, New York, NY (US)

(73) Assignee: ALPHAPOINTE, Kansas City, MO (US)

( * ) Notice: Subject to any disclaimer, the term of this patent is extended or adjusted under 35 U.S.C. 154(b) by 1192 days.

(21) Appl. No.: 17/560,027

(22) Filed: Dec. 22, 2021

(65) Prior Publication Data

US 2022/0110636 A1 Apr. 14, 2022

Related U.S. Application Data

(63) Continuation-in-part of application No. 16/250,896, filed on Jan. 17, 2019, now Pat. No. 11,207,077.

(Continued)

(51) Int. Cl.
*A61B 17/132* (2006.01)

(52) U.S. Cl.
CPC ...... *A61B 17/1327* (2013.01); *A61B 17/1325* (2013.01)

(58) Field of Classification Search
CPC ............ A61B 17/1325; A61B 17/1322; A61B 17/135; A61B 17/1327;

(Continued)

(56) References Cited

U.S. PATENT DOCUMENTS 3,570,496 A * 3/1971 Sachs ................. A61B 17/1325 606/203
5,234,459 A * 8/1993 Lee ...................... A61B 17/135 606/202

(Continued)

FOREIGN PATENT DOCUMENTS

| | | |
|---|---|---|
| CN | 205729433 U | 11/2016 |
| JP | 2007196018 A | 8/2007 |
| WO | 2019143855 A1 | 7/2019 |

OTHER PUBLICATIONS

"International Preliminary Report on Patentability received for PCT Application No. PCT/US2019/014071,Report issued on Jul. 21, 2020 mailed on Jul. 30, 2020".

(Continued)

*Primary Examiner* — Elizabeth Houston
(74) *Attorney, Agent, or Firm* — Kutak Rock LLP; Brian L. Main

(57) ABSTRACT

Apparatus, methods, and systems for hemorrhage control and pelvic stabilization are provided. The hemorrhage control plate includes a baseplate and a bulbous node extending outwardly. The bulbous node is positioned against a patient's body at a location where pressure is desired. The device is used in connection with a tourniquet to occlude blood flow at a hemorrhage site. The device is configured to attach to the tourniquet.

23 Claims, 7 Drawing Sheets

Related U.S. Application Data

(60) Provisional application No. 62/618,484, filed on Jan. 17, 2018.

(58) Field of Classification Search
CPC ........ A61B 2017/12004; A61B 17/132; A61B 2017/00477; A61B 2017/00526; A61H 39/04; A61H 2201/0119; A61H 2201/0157; A61H 2201/1695; A61F 5/30
See application file for complete search history.

(56) References Cited

U.S. PATENT DOCUMENTS

| | | | | |
|---|---|---|---|---|
| 5,307,811 | A | 5/1994 | Sigwart et al. | |
| 5,695,520 | A | 12/1997 | Bruckner et al. | |
| D815,289 | S | 4/2018 | Evers et al. | |
| D919,815 | S | 5/2021 | Ohashi et al. | |
| 11,207,077 | B2 | 12/2021 | Kosiorek et al. | |
| D974,564 | S | 1/2023 | Stafford | |
| 2002/0007195 | A1 | 1/2002 | Wexler | |
| 2013/0267994 | A1 * | 10/2013 | Crowder ............ | A61B 17/1325 606/203 |
| 2015/0094756 | A1 * | 4/2015 | Kosiorek ........... | A61B 17/1322 29/428 |
| 2016/0095605 | A1 * | 4/2016 | Maris ................... | A61B 5/7278 606/201 |
| 2016/0287262 | A1 | 10/2016 | Kirchner et al. | |
| 2019/0216469 | A1 | 7/2019 | Kosiorek | |

OTHER PUBLICATIONS

"Non-Final Action received for U.S. Appl. No. 16/250,896 , Mailed on Jan. 11, 2021".

"Notice of Allowance received for U.S. Appl. No. 16/250,896, Mailed on Aug. 23, 2021."

Kosiorek, Christopher B., "International Search Report and Written Opinion Received Of PCT. Application No. PCT/US19/14071 mailed on May 9, 2019, pp. 14".

"Notice of Allowance received for U.S. Appl. No. 29/677,184, Mailed on Jan. 26, 2023."

* cited by examiner

HEMORRHAGE CONTROL PLATE APPARATUS, SYSTEMS, AND METHODS

CROSS-REFERENCE TO RELATED APPLICATIONS

This is a continuation-in-part application of U.S. patent application Ser. No. 16/250,896, filed Jan. 17, 2019 and now U.S. Pat. No. 11,207,077, which claims priority pursuant to 35 U.S.C. 119(e) to U.S. Provisional Patent Application Ser. No. 62/618,484, filed Jan. 17, 2018, the entire disclosures of which are incorporated herein by reference.

FIELD

The present invention relates generally to apparatuses and related systems and methods configured to control blood loss in a patient. More specifically, the present invention is concerned with a small, lightweight, easy-to-use device that can be used to apply direct pressure to a major artery such as the femoral artery or axillary artery.

BACKGROUND

Approximately 80 percent of potentially survivable casualties on today's battlefield nevertheless result in mortality due to uncontrolled hemorrhage. Devices that control hemorrhage on the battlefield early in the continuum of care may likely increase the survivability of combat casualties. The present inventive concept has been developed and intended to be carried in the Individual First Aid Kit (IFAK), and Combat Lifesaver (CLS) bags for temporary control of hemorrhage. In some embodiments, the present inventive concept is used in conjunction with a tourniquet such as described in U.S. Pat. Pub. No. US20150094756 to control hemorrhage in compressible, non-tourniquetable regions.

The Wake Forest School of Medicine human cadaver hemostasis model was used to test the efficacy of the present inventive concept. This testing platform uses a pulsatile peristaltic pump to produce realistic constant blood flow within the arteries of a fresh unembalmed human cadaver. Testing hemostatic devices and procedures using intact fresh human tissue has some advantages over alternative live tissue models when a mechanical device is employed to reduce arterial flow rates.

Authentic human anatomy is an important requirement for validating the efficacy of hemorrhage control devices when an external control device is applied to control flow in the external iliac artery at or above the inguinal ligament where peripheral limb tourniquet application cannot be used. In this feasibility study, one fresh human cadaver was used with peristaltic tubing inserted and sealed within the thoracic aorta. An external peristaltic pump was used to deliver fluid through arteries in the descending abdomen, pelvis and limbs of the cadaver with a constant peristaltic speed and constant arterial flow rate consistent with physiological levels. The right popliteal arteries were cut in order to observe dynamic changes in downstream arterial flow rates from fluid pumped through the thigh before, during and after the application of hemorrhage control devices with constant peristaltic pumping. Successful application was measured by arresting of flow through the external iliac artery by observing the flow rate at the exposed popliteal artery.

The human hemostatic testing model developed at the Wake Forest School of Medicine was used to demonstrate the capacity of the present inventive concept to stop arterial flow when applied to the external iliac artery. The present inventive concept completely stopped blood flow and arterial pressure with minimal turns of the tourniquet windlass when the device was applied to the surface of the cadaver just above the inguinal ligament. The present inventive concept controlled arterial flow through the external iliac in 40 tests on 4 cadaver models.

The present inventive concept effectively stopped flow in the external iliac artery. It is configured to control hemorrhage.

SUMMARY

The present inventive concept comprises a bulbous node extending outwardly away from a base plate. The bulbous node includes a convex surface that is configured to be position against a patient's body. When the bulbous node is placed on a patient's body aligned with an artery and pressure is applied, the convex surface applies pressure directly on the patient's artery, preferably sufficient to stop blood flow or otherwise control hemorrhage. In some embodiments, the present inventive concept is formed of a strong plastic material. In other embodiments, it is formed of metal. In some embodiments, the plate includes a tab on opposite ends. In some embodiments, the opposing tabs are sized and shaped to mate with corresponding slots in the carriage of the tactical mechanical tourniquet disclosed in U.S. Pat. Pub. No. US20150094756. In some embodiments, insertion of the tabs into the slots creates a bend in the base plate creating an arc away from the carriage and toward the patient's body, which provides for an increase in strength and rigidity and allows for use across a larger patient population.

The present inventive concept provides for mechanical hemorrhage control. External environmental changes such as temperature changes or changes in barometric pressure do not affect the functionality or use of the present inventive concept.

The present inventive concept is used for hemorrhage control on upper or lower extremities. Two hemorrhage control plates, one on each femoral artery, are used simultaneously to stop blood flow in the event of lower extremity bilateral amputation. The present inventive concept is used to cease radial pulse in an upper extremity. The present inventive concept is used to cease popliteal pulse and/or tibialis posterior pulse in a lower extremity.

Current clinical practice guidelines strongly recommend the use of a pelvic stabilizing device in patients who require hemorrhage control in the inguinal areas. The mechanisms of injury that create the conditions requiring hemorrhage control often create secondary injuries that are unseen to the naked eye. Pelvic stabilization devices serve to both manage patient comfort and minimize exacerbation of any underlying musculoskeletal injuries. To meet the generally acceptable criteria for pelvic stabilization, the device should have a minimum width of 2 inches and secure circumferentially around the pelvic girdle.

The foregoing and other objects are intended to be illustrative of the invention and are not meant in a limiting sense. Many possible embodiments of the invention may be made and will be readily evident upon a study of the following specification and accompanying drawings comprising a part thereof. Various features and subcombinations of invention may be employed without reference to other features and subcombinations. Other objects and advantages of this invention will become apparent from the following description taken in connection with the accompanying drawings, wherein is set forth by way of illustration and example, an embodiment of this invention and various features thereof.

BRIEF DESCRIPTION OF THE DRAWINGS

A preferred embodiment of the invention, illustrative of the best mode in which the applicant has contemplated applying the principles, is set forth in the following description and is shown in the drawings and is particularly and distinctly pointed out and set forth in the appended claims.

DETAILED DESCRIPTION

Figure 1:
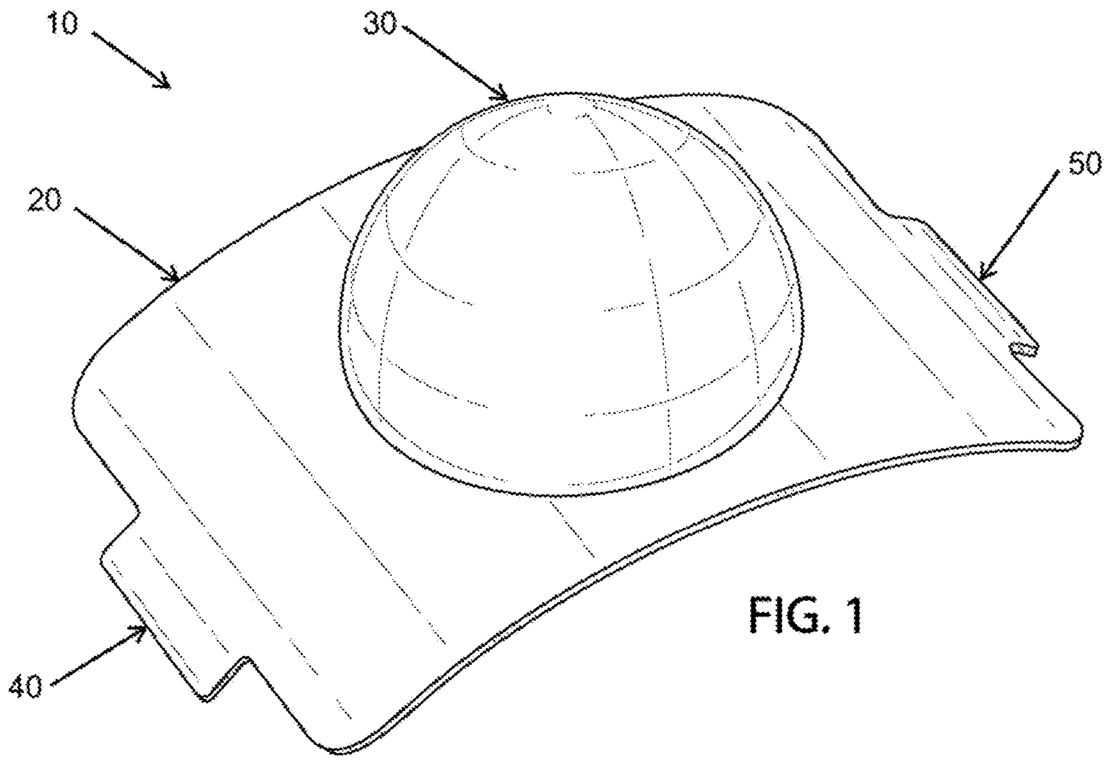
FIG. 1 is a top perspective view of an embodiment of the present invention.
Figure 2:
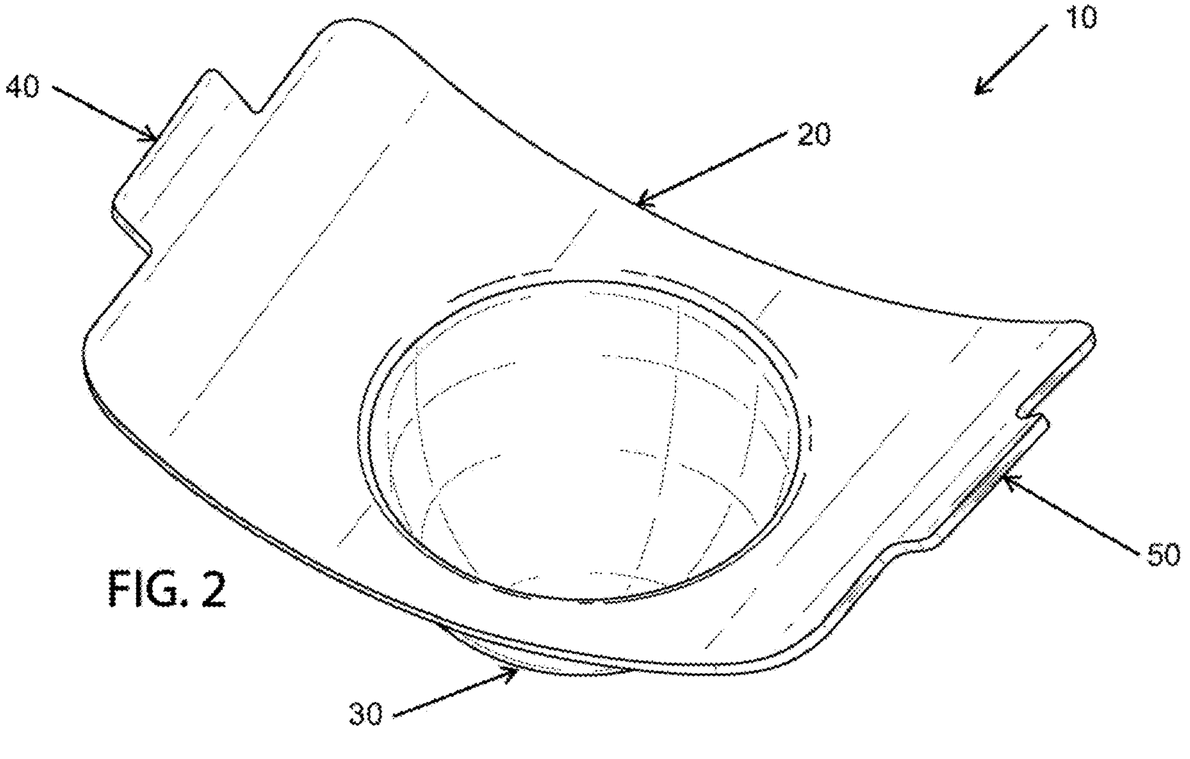
FIG. 2 is a bottom perspective view of the embodiment shown in FIG. 1.

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense.

In this description, references to "one embodiment," "an embodiment," or "embodiments" mean that the feature or features being referred to are included in at least one embodiment of the technology. Separate references to "one embodiment," "an embodiment," or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the present technology can include a variety of combinations and/or integrations of the embodiments described herein.

The present inventive concept is directed to a hemorrhage control plate apparatus, systems of tourniquets and hemorrhage control plates, and methods of use. Referring to FIGS. 1 through 8, various embodiments of the present inventive concept are shown. In some embodiments, the present inventive concept is a hemorrhage control plate apparatus 10. The hemorrhage control plate 10 includes a baseplate 20 and a bulbous node 30 extending outwardly from the baseplate 20. In some embodiments, the bulbous node 30 is a semispherical or otherwise-shaped protrusion. In some embodiments, the bulbous node 30 includes a convex surface. In some embodiments, the bulbous node 30 is hollow. In some embodiments, the bulbous node 30 is configured to be positioned against a patient's body such that the bulbous node 30 aligns with a wound of the patient. In some embodiments, the hemorrhage control plate 10 is made of a plastic material. In some embodiments, the hemorrhage control plate 10 is made of a metal material.

In some embodiments, the hemorrhage control plate 10 includes a first insert tab 40 positioned at a first end of the baseplate 20. In some embodiments, the hemorrhage control plate 10 includes a second insert tab 50 positioned at a second end of the baseplate 20. In some embodiments, the first insert tab 40 is positioned opposite the second insert tab 50. Or in other words, the first end of the baseplate 20 is opposite the second end of the baseplate 20.

Figure 3:
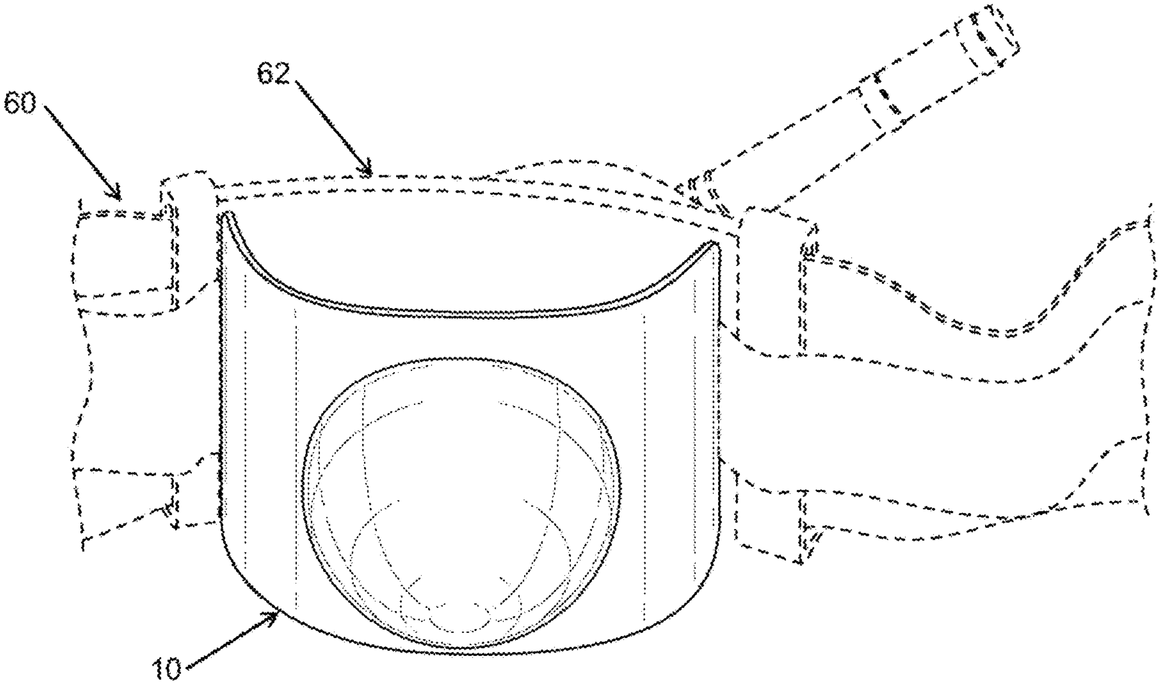
FIG. 3 is a perspective view of the embodiment shown in FIG. 1, with tourniquet shown in broken lines.
Figure 4:
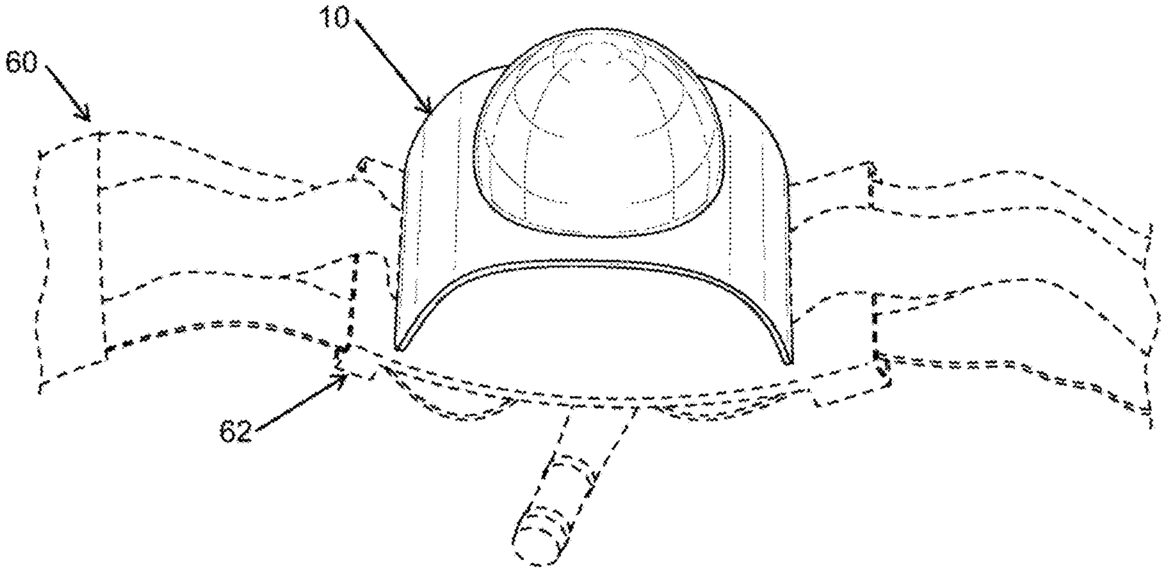
FIG. 4 is a perspective view of the embodiment shown in FIG. 1, with tourniquet shown in broken lines.
Figure 8:
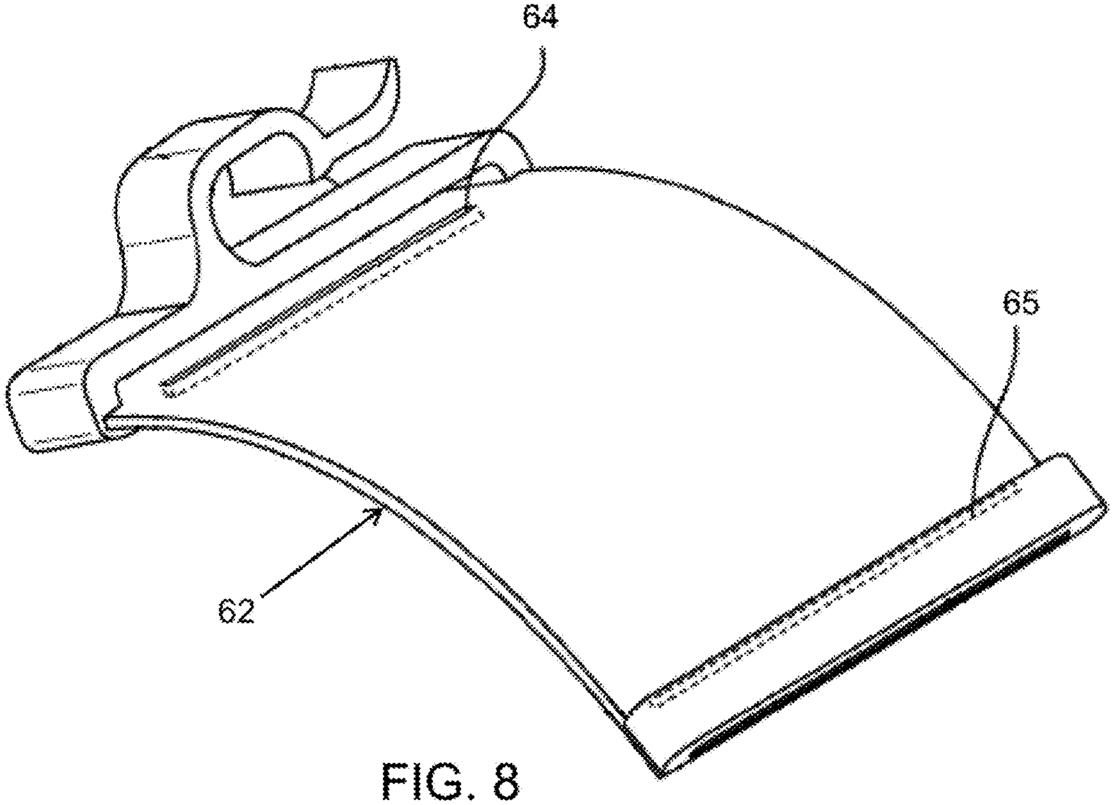
FIG. 8 is a perspective view of a carriage of the tourniquet of FIG. 3.
Figure 9:
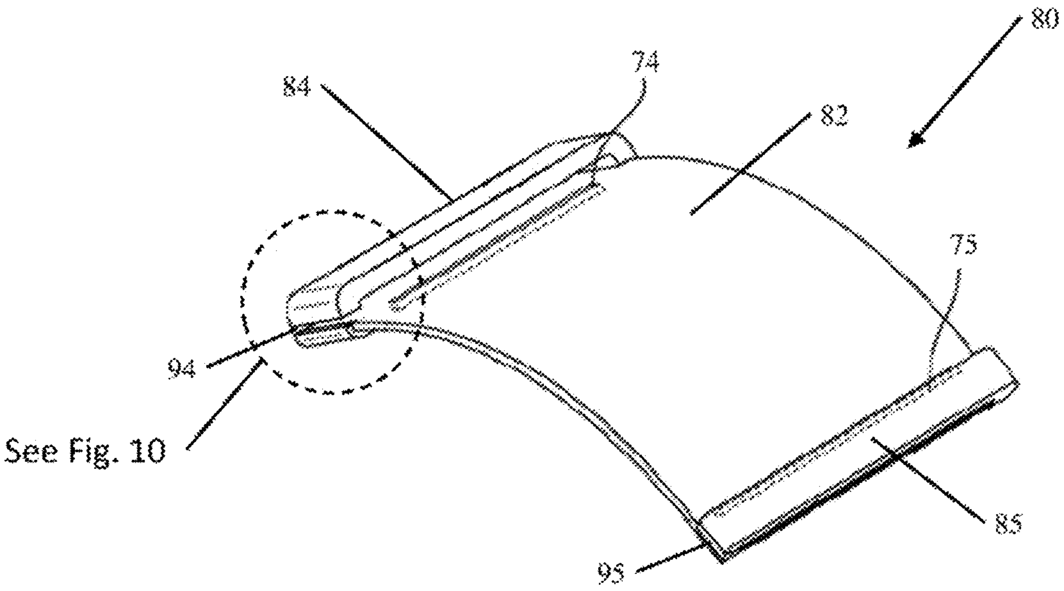
FIG. 9 is a perspective view of a clip assembly of an embodiment of the present invention, the clip being configured to engage with a tourniquet.
Figure 10:
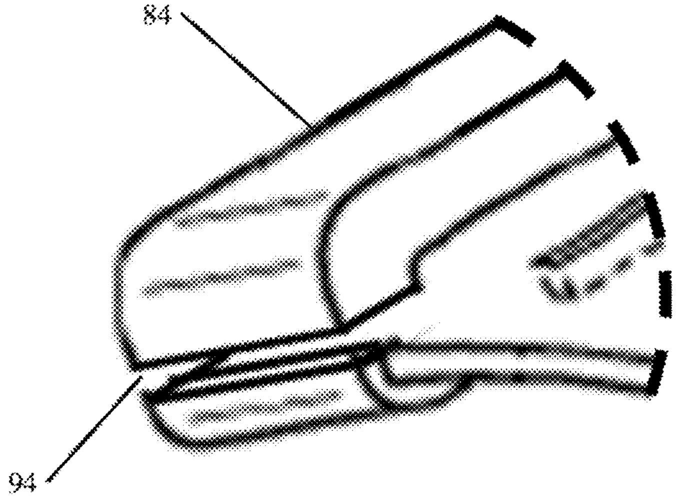
FIG. 10 is a partial view of the clip assembly of FIG. 9 shown in an enlarged scale.
Figure 11:
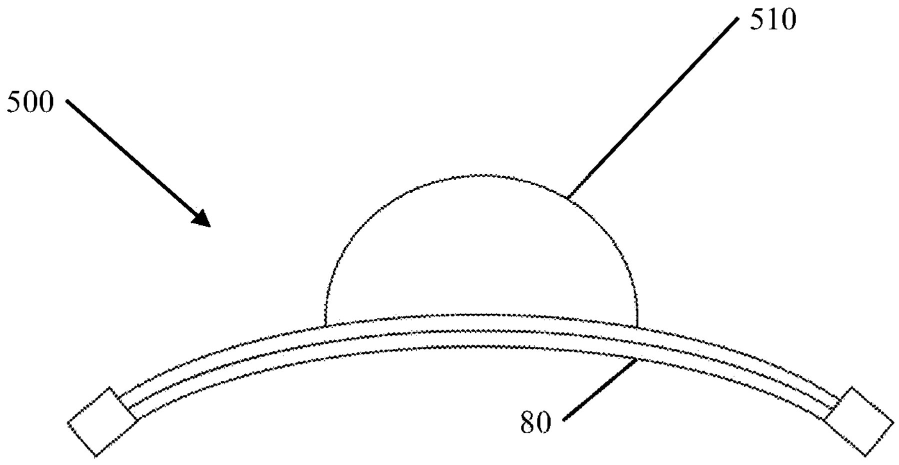
FIG. 11 is a side elevation view of a hemorrhage control plate and a clip assembly of an embodiment of the present invention, each shown in a respective nesting configuration.
Figure 12:
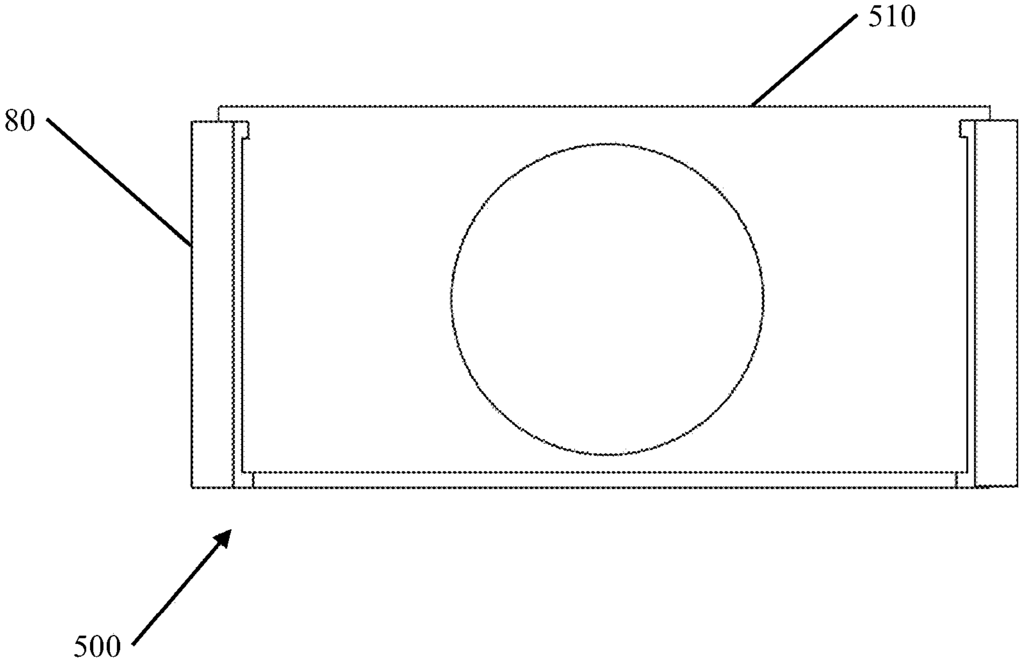
FIG. 12 is a top elevation view of the hemorrhage control plate and clip assembly of FIG. 11.
Figure 13:
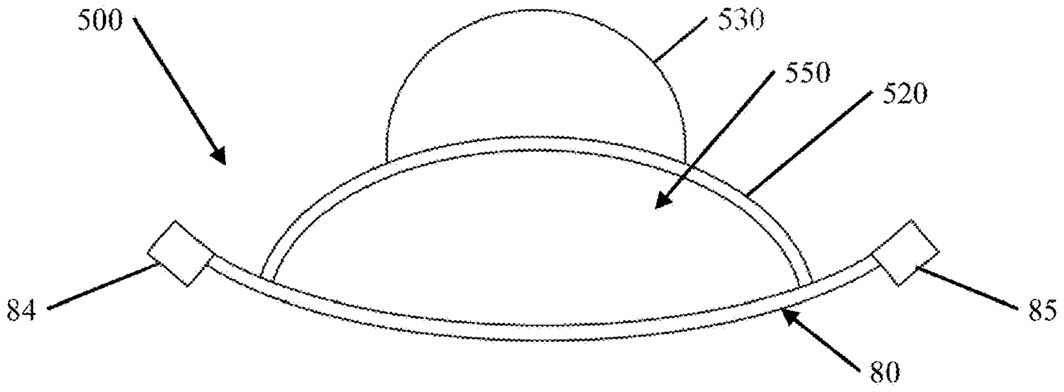
FIG. 13 is a side elevation view of the hemorrhage control plate and clip assembly of FIG. 11, the hemorrhage control plate shown in an engaged configuration relative to the clip assembly.
Figure 14:
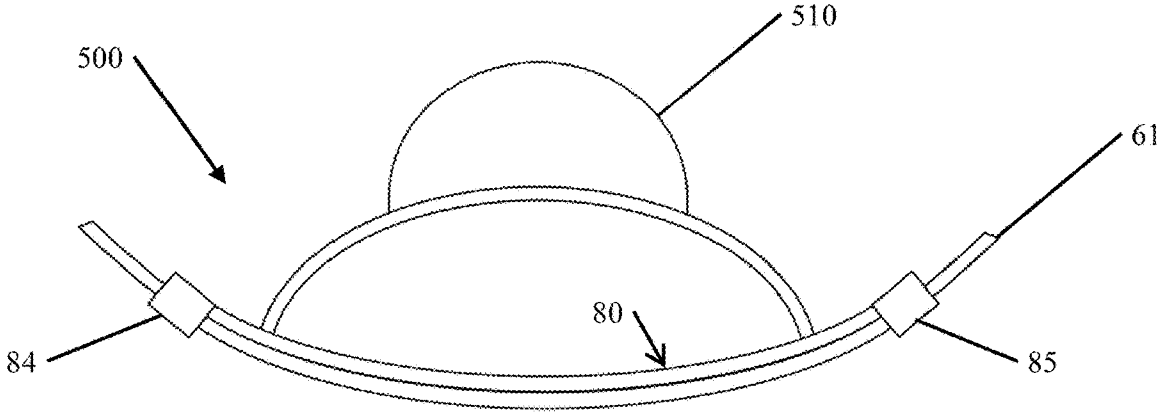
FIG. 14 is a side elevation view showing the clip assembly of FIG. 13 engaged with a tourniquet body of a tourniquet.
Figure 15:
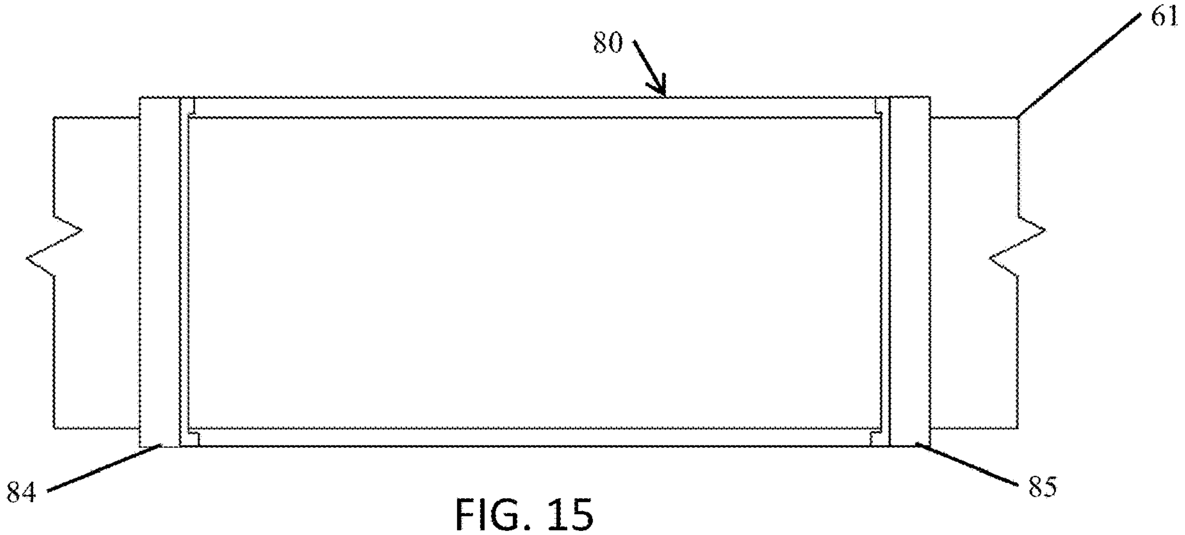
FIG. 15 is a bottom view of the configuration shown in FIG. 14, the hemorrhage control plate being concealed from view.

Referring to FIGS. 3, 4, and 8, in some embodiments, the hemorrhage control plate 10 is configured to be attached to a tourniquet 60 in any manner now known or later developed. In some embodiments, the baseplate 20 is configured to be attached to a tourniquet 60. In some embodiments, the first insert tab 40 is configured to mate with a corresponding first slot 64 associated with the tourniquet 60, such as a slot defined by a carriage 62 of the tourniquet 60. In some embodiments, the second insert tab 50 is configured to mate with a corresponding second slot 65 associated with the tourniquet 60, such as a slot defined by a carriage 62 of the tourniquet 60. In some embodiments, the first insert tab 40 is configured to mate with the first slot 64 while the second insert tab 50 is mated with the second slot 65, thereby moving the hemorrhage control plate 10 from a disengaged configuration to secured configuration relative to the tourniquet 60.

In some embodiments, the hemorrhage control plate is biased towards a deformed configuration when the hemorrhage control plate is in the engaged configuration relative to the tourniquet 60. In some such embodiments, the first 40 and second 50 insert tabs are positioned first and second distances away from each other when the hemorrhage control plate 10 is in the disengaged and engaged configurations, respectively. In some such embodiments, the first distance is greater than the second distance such that the bulbous node 30 is biased away from the tourniquet 60 when the hemorrhage control plate 10 is in the engaged configuration. In some embodiments, the distance between the first 64 and second 65 slots of the tourniquet 60 is less than a distance between the first 40 and second 50 insert tabs of the hemorrhage control plate 10 such that a preload is created in the hemorrhage control plate 10 and/or the tourniquet 60 when the hemorrhage control plate 10 is moved into engagement with the tourniquet. In some such embodiment, the preload results in the baseplate 20 of the hemorrhage control plate 10 being bent in an arcuate manner.

Figure 5:
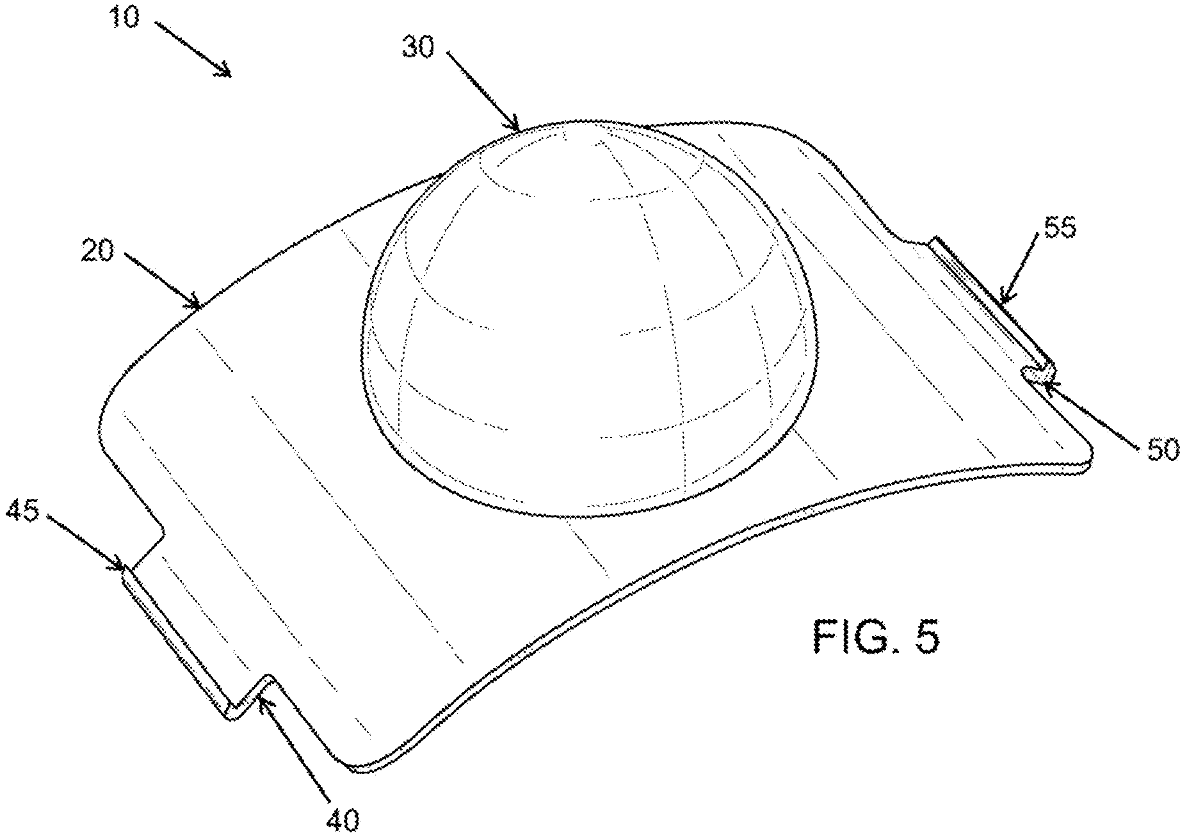
FIG. 5 is a top perspective view of an embodiment of the present invention.
Figure 6:
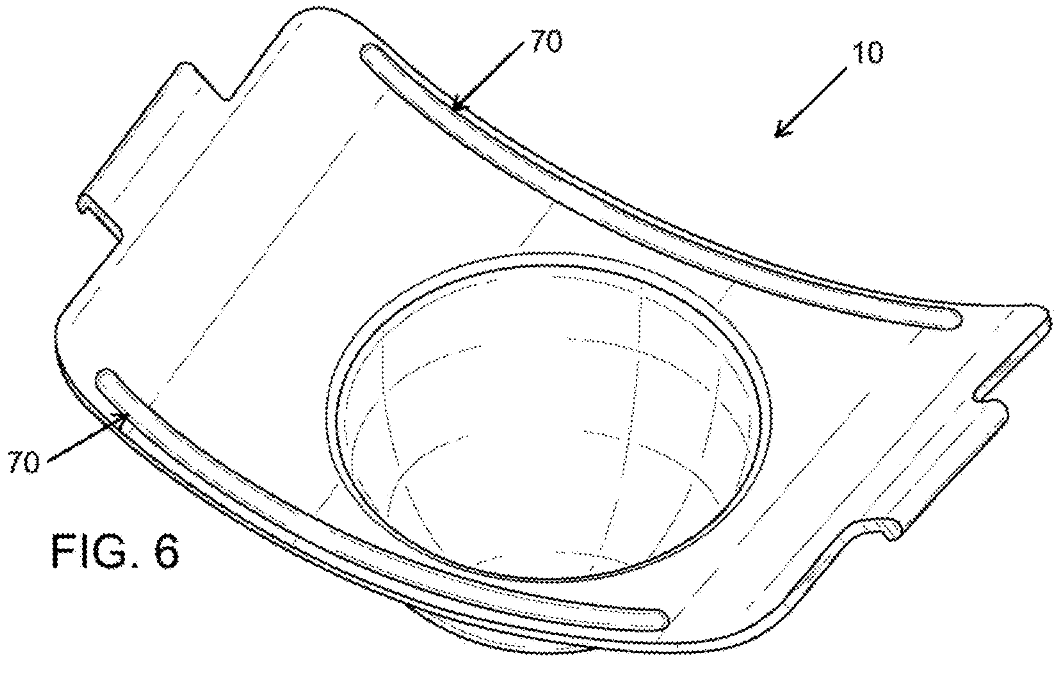
FIG. 6 is a bottom perspective view of the embodiment shown in FIG. 5.
Figure 7:
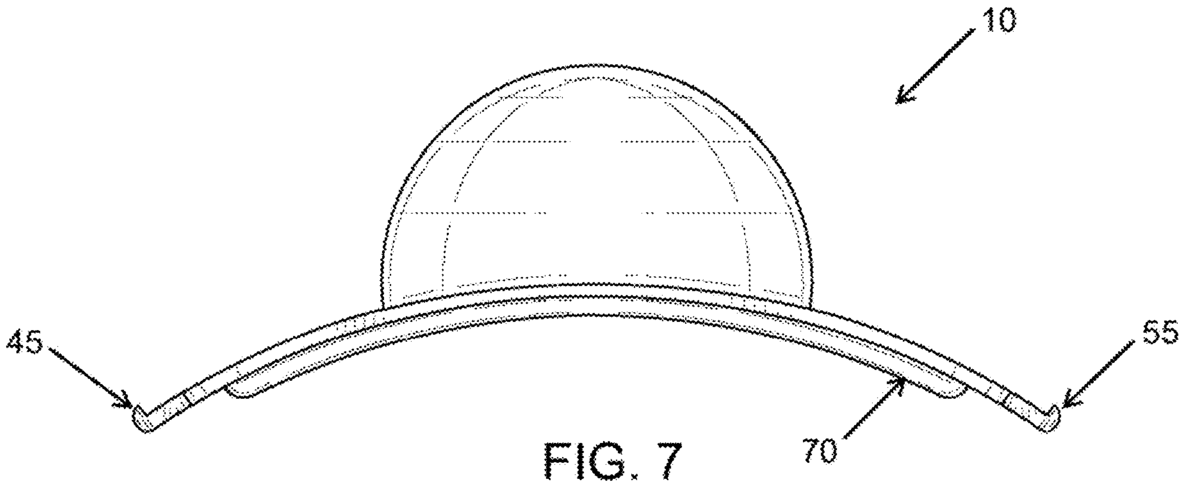
FIG. 7 is a left-side view of the embodiment shown in FIG. 5, the right-side view being a mirror image.

Referring to FIGS. 5 through 7, in some embodiments, at least one of the insert tabs 40 or 50 includes a locking end spur 45 or 55. The locking end spur 45 or 55 securely attaches the baseplate 20 to the tourniquet 60 to hold the hemorrhage control plate 10 in place, so the insert tabs 40 or 50 do not inadvertently release from corresponding slots 64 and 65.

In some embodiments, the baseplate 20 also includes one or more reinforcing rib 70, which may also be referred to as a truss or buttress. In some embodiments, the baseplate 20 includes two reinforcing ribs 70, each configured to extend lengthwise along the long axis of the hemorrhage control plate 10. In some embodiments, the reinforcing rib 70 is located near the side edge of the baseplate 20. In some embodiments, the reinforcing rib 70 is configured to be aligned in parallel with the length of the tourniquet 60 when the hemorrhage control plate 10 is attached to the tourniquet 60. The one or more reinforcing rib 70 provides stronger structural integrity when the baseplate 20 is bent in an arcuate manner.

Referring to FIGS. 3, 4, and 8, in some embodiments, the baseplate 20 is configured to bend temporarily and become arcuate when the baseplate 20 is attached to the tourniquet. In some embodiments, the baseplate 20 is configured to bend temporarily and become arcuate when the first insert tab 40 is mated with the corresponding first slot 64 of the tourniquet 60 and the second insert tab 50 is mated with the corresponding second slot 65 of the tourniquet 60. In some embodiments, the bulbous node 30 is configured to be positioned against a patient's body such that the bulbous node 30 aligns with an artery and/or wound associated with the patient's body. In some embodiments, the bulbous node 30 is configured to apply increased localized pressure to the patient's body when the tourniquet 60 is tightened. In some embodiments, the bulbous node 30 is configured to maintain pressure on the patient's body when the tourniquet 60 is tightened.

The present inventive concept also includes various methods of use. In some embodiments, the method of use of a hemorrhage control plate 10 includes positioning at least one hemorrhage control plate 10 against a patient's body, such that a bulbous node 30 extending outwardly from a baseplate 20 of the hemorrhage control plate 10 is aligned with a corresponding artery and/or wound associated with the patient's body. In some embodiments, pressure is applied and/or maintained to the hemorrhage control plate 10, such that the bulbous node 30 applies and/or maintains pressure. In some embodiments, the methods of use also include attaching the hemorrhage control plate 10 to a tourniquet 60. In some embodiments, the step of attaching the hemorrhage control plate 10 to a tourniquet 60 includes mating the first insert tab 40 with the corresponding first slot 64 in the tourniquet 60 and mating the second insert tab 50 with the corresponding second slot 65 in the tourniquet 60. In some embodiments, the method also includes bending, temporarily, the baseplate 20 such that it becomes arcuate when the insert tabs 40 and 50 are mated with their respective corresponding slots 64 and 65. In some embodiments, the method also includes tightening the tourniquet 60 to apply and/or maintain pressure to the hemorrhage control plate 10, which also applies and/or maintains pressure at the bulbous node 30 to the desired area of the patient's body. In some embodiments, at least one of the insert tabs, preferably both, includes a locking end spur. In some embodiments, the method also includes locking the locking end spur of the first or second insert tab(s) into the corresponding first or second slot(s), respectively.

Sometimes, as the tourniquet 60 is tightened, the hemorrhage control plate 10 tends to roll such that hemorrhage control plate 10 is no longer properly aligned with the desired area. In some embodiments, the baseplate 20 has two sides opposite one another and positioned between the two ends and at least one of these two sides include a protrusion configured to reduce, mitigate, or otherwise eliminate this type of roll.

The present inventive concept also includes various tourniquet and hemorrhage control plate systems. In some embodiments, the system includes a tourniquet 60 configured to receive a hemorrhage control plate 10. The hemorrhage control plate 10 includes a baseplate 20 and a bulbous node 30 extending outwardly from the baseplate 30. The bulbous node 30 is configured to be positioned against a patient's body such that the bulbous node 30 aligns with a desired area of the patient's body. In some embodiments, the hemorrhage control plate 10 is made of a plastic material. In some embodiments, the hemorrhage control plate 10 is made of a metal material. In some embodiments, the system is configured such that the first insert tab 40 is positioned at the first end of the baseplate 20 and the second insert tab 50 is positioned at the second end of the baseplate 20. In some embodiments, the first insert tab 40 is configured to mate with the corresponding first slot 64 in the tourniquet 60 and the second insert tab 50 is configured to mate with the corresponding second slot 65 in the tourniquet 60. In some embodiments, the baseplate 20 is configured to bend, temporarily, and become arcuate when the first and second insert tabs 40 and 50 are mated with the corresponding first and second slots 64 and 65 in the tourniquet 60. In some embodiments, the tourniquet 60 is tightened to apply pressure to the hemorrhage control plate 10, which also applies pressure at the bulbous node 30 to the corresponding area of the patient's body.

Referring to FIGS. 9-15, some embodiments of the present invention utilize a clip assembly 80 for securing the hemorrhage control plate to 10 to a tourniquet 60. In some embodiments, the clip assembly 80 includes opposed first 84 and second 85 clip members and a clip plate 82 extending therebetween. In some such embodiments, the clip plate 82 defines first 74 and second 75 slots for receiving respective first 40 and second 50 insert tabs of the hemorrhage control plate 10. In some embodiments, the first insert tab 40 is configured to mate with the first slot 74 while the second insert tab 50 is mated with the second slot 75, thereby moving the hemorrhage control plate 10 from a disengaged configuration to secured configuration relative to the clip assembly 80.

In some embodiments, the hemorrhage control plate is biased towards a deformed configuration when the hemorrhage control plate is in the engaged configuration relative to the clip assembly 80. In some such embodiments, the first 40 and second 50 insert tabs are positioned first and second distances away from each other when the hemorrhage control plate is in the disengaged and engaged configurations, respectively. In some such embodiments, the first distance is greater than the second distance such that the bulbous node 30 is biased away from the clip assembly 80 when the hemorrhage control plate is in the engaged configuration. In some embodiments, the distance between the first 74 and second 75 slots of the clip assembly is less than a distance between the first 40 and second 50 insert tabs of the hemorrhage control plate such that a preload is created in the hemorrhage control plate 10 and/or the clip assembly 80 when the hemorrhage control plate 10 is moved into engagement with the clip assembly 80. In some such embodiments, the preload results in the baseplate 20 of the hemorrhage control plate 10 being bent in an arcuate manner.

In some embodiments, respective proximal ends of the first 84 and second 85 clip members are coupled to respective first and second ends of the clip plate 82 while respective distal ends of the first 84 and second 85 clip members are displaced from the clip plate 85, thereby defining respective first 94 and second 95 gaps, such gaps being configured to facilitate moving the clip assembly 80 in and out of engagement with the tourniquet 60. In some embodiments, the clip assembly 80 includes one or more securing feature, now known or later developed, for securing the clip assembly 80 to the tourniquet 60, thereby securing the hemorrhage control plate 10 relative to the tourniquet 60 when the hemorrhage control plate 10 is in the engage configuration relative to the clip assembly 80.

Referencing FIGS. 11-15, the embodiment shown is a hemorrhage control system 500 that includes a hemorrhage control plate 510 having a pressure applicator 530 and a support portion 520 for supporting the pressure applicator 530. The hemorrhage control system 500 also includes a clip assembly 80 that functions as a base portion for engaging the hemorrhage control system 500 with a tourniquet body 61 of a tourniquet assembly. In some embodiments, the pressure applicator 530 defines a bulbous shape, such as the bulbous node 30 of a the hemorrhage control plate of various other embodiments of the present invention, the bulbous shape being configured for applying pressure to a desired area. In some embodiments, the support portion 520 comprises a plurality of thin plate members, such as first and second portions of the baseplate 20 of the hemorrhage control plate 10 of the various other embodiments, at least some of the plate members being configured to maintain displacement of the pressure applicator 530 from the base portion during use. In this way, the hemorrhage control system 500 defines an open void 550 between the base portion and the pressure applicator 530, thereby facilitating digital application of pressure and/or digital adjustment of the location of the system.

In some embodiments, the base portion is configured to engage with a tourniquet, thereby facilitating generation of pressure by tightening the tourniquet. In some embodiments, the base portion is configured to slide along a first region of said tourniquet, such as by sliding a tourniquet body 61 within gaps 94, 95 defined by clip members 84, 85 of the base portion. In some embodiments, the support portion 520 is coupled to the base portion at opposed first and second locations. In some such embodiments, the first and second locations are displaced longitudinally along a first portion of the first region of the tourniquet body 61.

In some embodiments, the base portion is configured to engage with a tourniquet, thereby facilitating generation of pressure by tightening the tourniquet. In some embodiments, the base portion is configured to slide along a first region of said tourniquet, such as by sliding a tourniquet body within gaps defined by clip members of the base portion. In some embodiments, the support portion is coupled to the base portion at opposed first and second locations. In some such embodiments, the first and second locations are displaced longitudinally along a first portion of the first region of the tourniquet body.

While the present general inventive concept has been shown in the drawings and fully described above with particularity and detail in connection with what is presently deemed to be the most practical and preferred embodiment (s) of the invention, it will be apparent to those of ordinary skill in the art that many modifications thereof may be made without departing from the principles and concepts set forth herein, including, but not limited to, variations in size, materials, shape, form, function and manner of operation, assembly and use.

It is also to be understood that the following claims are intended to cover all of the generic and specific features of the invention herein described, and all statements of the scope of the invention which, as a matter of language, might be said to fall there between. Hence, the proper scope of the present general inventive concept should be determined only by the broadest interpretation of the appended claims so as to encompass all such modifications as well as all relationships equivalent to those illustrated in the drawings and described in the specification.

Finally, it will be appreciated that the purpose of the annexed Abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. Accordingly, the Abstract is neither intended to define the invention or the application, which only is measured by the claims, nor is it intended to be limiting as to the scope of the invention in any way.

What is claimed is:

1. A hemorrhage control system that is movable between a stowed configuration and a deployed configuration, the hemorrhage control system comprising:

a pressure applicator configured for applying pressure to a location on a patient when the system is in the deployed configuration;

a base portion displaced from said pressure applicator when the system is in the deployed configuration; and a support portion extending between said pressure applicator and said base portion when the system is in the deployed configuration, wherein said base portion comprises opposed first and second clip members, wherein opposed distal ends of said support portion are received by said first and second clip members, respectively, when the system is in the stowed configuration, and wherein said support portion is engaged with said base portion, but displaced from said first and second clip members, when the system is in the deployed configuration.

2. The hemorrhage control system of claim 1, wherein said pressure applicator is a bulbous node.

3. The hemorrhage control system of claim 1, wherein said support portion is configured to nest with the base portion in a concave manner.

4. The hemorrhage control system of claim 1, wherein the base portion defines a first slot and a second slot, said first slot being displaced from said second slot.

5. The hemorrhage control system of claim 4, wherein said support portion comprises opposed first and second insert tabs extending from respective distal ends of said support portion, said first and second insert tabs of said support portion being received by said first and second slots, respectively, of said base portion when the system is in the deployed configuration.

6. The hemorrhage control system of claim 1, further comprising a tourniquet having a tourniquet body, said base portion being configured to selectively engage with said tourniquet body.

7. The hemorrhage control system of claim 6, wherein said first clip member is configured to slide in and out of engagement with said tourniquet body, thereby moving said base portion between engaged and disengaged configurations, respectively.

8. The hemorrhage control system of claim 7, wherein said first clip member is perpendicular to said tourniquet body when said base portion is in its engaged configuration.

9. The hemorrhage control system of claim 8, wherein said first clip member defines a gap, said gap being configured to receive said tourniquet body when said base portion is in its engaged configuration.

10. The hemorrhage control system of claim 7, wherein said first clip member defines a gap, said gap being configured to receive said tourniquet body when said base portion is in the engaged configuration.

11. The hemorrhage control system of claim 10, wherein said tourniquet body is configured to slide through said gap, thereby facilitating changing the positioning of said pressure applicator along a first region of said tourniquet body.

12. The hemorrhage control system of claim 11, wherein said support portion is configured to inhibit movement of said pressure applicator towards said base portion as said tourniquet is tightened, thereby facilitating utilization of a tourniquet to apply pressure to the location on the patient.

13. The hemorrhage control plate of claim 12, wherein the displacement of said pressure applicator from said base portion defines an open void, the open void being configured to receive fingers of a hand, thereby facilitating digital application of pressure to the location on the patient.

14. A method of using a hemorrhage control system to apply pressure to a location on a patient, the method comprising:

moving the system from a stowed configuration to a deployed configuration;

positioning a pressure applicator of the system against the location on the patient;

biasing a base portion of the system towards the location on the patient, thereby generating pressure at the location on the patient; and utilizing a support portion of the system to inhibit movement of the base portion relative to the pressure applicator, wherein the support portion extends between the pressure applicator and the base portion when the system is in the deployed configuration, wherein the base portion comprises opposed first and second clip members, wherein opposed distal ends of the support portion are received by the first and second clip members, respectively, when the system is in the stowed configuration, wherein moving the system from the stowed configuration to the deployed configuration comprises:

sliding the support portion away from the base portion so that the distal ends of the support portion are no longer received by the first and second clip members of the base portion; and engaging the support portion with the base portion such that the support portion is displaced from the first and second clip members.

15. The method of claim 14, wherein the pressure applicator is a bulbous node.

16. The method of claim 14, further comprising constricting a tourniquet body of a tourniquet, thereby biasing the base portion towards the location on the patient.

17. The method of claim 16, further comprising engaging the first clip member of the base portion with the tourniquet body of the tourniquet, thereby moving the base portion to an engaged configuration, wherein the first clip member is perpendicular to the tourniquet body when the base portion is in the engaged configuration.

18. The method of claim 17, wherein the first clip member defines a gap, the gap being configured to receive the tourniquet body when the base portion is in the engaged configuration, and wherein the tourniquet body is configured to slide within the gap, thereby facilitating positioning of the pressure applicator along a first region of the tourniquet body.

19. The method of claim 18, further comprising:

extending fingers into an open void positioned between the base portion and the pressure applicator; and applying digital pressure to the hemorrhage control system, thereby applying pressure to the location on the patient.

20. A method of making a hemorrhage control system that is moveable between a stowed configuration and a deployed configuration, the method comprising:

positioning a pressure applicator at a first location, the pressure applicator being configured to apply pressure to a location on a patient when the system is in the deployed configuration;

positioning a base portion at a second location such that the base portion is displaced from the pressure applicator when the system is in the deployed configuration;

extending a support portion between the pressure applicator and the base portion when the system is in the deployed configuration; and forming opposed first and second clip members on the base portion, wherein opposed distal ends of the support portion are configured to receive said first and second clip members, respectively, when the system is in the stowed configuration, and wherein the support portion is engaged with the base portion, but displaced from the first and second clip members, when the system is in the deployed configuration.

21. The method of claim 20, wherein said first clip member is configured to slide in and out of engagement with a tourniquet body of a tourniquet, thereby moving the base portion between engaged and disengaged configurations, respectively.

22. The method of claim 21, wherein the first clip member is perpendicular to the tourniquet body when the base portion is in its engaged configuration, and wherein the first clip member defines a gap, the gap being configured to receive the tourniquet body when the base portion is in its engaged configuration.

23. The method of claim 22, further comprising forming an open void between the base portion and the pressure applicator, the open void being configured to receive fingers of a hand, thereby facilitating digital application of pressure to the location on the patient.

* * * * *